United States Patent
Shelly et al.

(10) Patent No.: US 9,901,287 B2
(45) Date of Patent: Feb. 27, 2018

(54) PATIENT MONITORING AND EXCEPTION NOTIFICATION

(75) Inventors: Benjamin Irwin Shelly, Eindhoven (NL); Michael Thomas Kane, Eindhoven (NL); Gregory Delano Matthews, Eindhoven (NL); Heather Dawn Ressler, Eindhoven (NL); Duane Howard Carter, Jr., Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 707 days.

(21) Appl. No.: 13/994,364

(22) PCT Filed: Dec. 19, 2011

(86) PCT No.: PCT/IB2011/055781
§ 371 (c)(1),
(2), (4) Date: Jun. 14, 2013

(87) PCT Pub. No.: WO2012/085820
PCT Pub. Date: Jun. 28, 2012

(65) Prior Publication Data
US 2013/0267865 A1    Oct. 10, 2013

Related U.S. Application Data

(60) Provisional application No. 61/425,827, filed on Dec. 22, 2010.

(51) Int. Cl.
*A61B 5/08* (2006.01)
*A61B 5/00* (2006.01)
*A61M 16/00* (2006.01)

(52) U.S. Cl.
CPC .......... *A61B 5/0803* (2013.01); *A61B 5/0004* (2013.01); *A61B 5/0022* (2013.01); *A61B 5/08* (2013.01); *A61M 16/00* (2013.01); *A61B 5/4818* (2013.01); *A61B 5/7275* (2013.01); *A61B 2505/07* (2013.01)

(58) Field of Classification Search
None
See application file for complete search history.

(56) References Cited

U.S. PATENT DOCUMENTS

| | | | | |
|---|---|---|---|---|
| 4,671,297 | A * | 6/1987 | Schulze, Jr. | A61M 16/00 128/204.23 |
| 5,291,013 | A * | 3/1994 | Nafarrate | A61B 5/113 128/925 |
| 2003/0066528 | A1* | 4/2003 | Hill | A61M 16/00 128/204.18 |

(Continued)

FOREIGN PATENT DOCUMENTS

| WO | WO2006079152 A1 | 8/2006 |
|---|---|---|
| WO | WO2008135985 A1 | 11/2008 |
| WO | WO2009118737 A2 | 10/2009 |

*Primary Examiner* — Jacqueline Cheng
*Assistant Examiner* — Jairo Portillo
(74) *Attorney, Agent, or Firm* — Michael W. Haas

(57) ABSTRACT

A monitoring system is used to measure various parameters of the sleep, respiration, and/or other bodily functions of a subject. One or more metrics are calculated that quantify deviation from the mean, trends, changes over time, and/or other changes in the parameters. The metrics are used to generate notifications of these changes that can be conveyed to caregivers and/or other users.

9 Claims, 2 Drawing Sheets

(56) References Cited

U.S. PATENT DOCUMENTS

| | | | | |
|---|---|---|---|---|
| 2003/0121519 A1* | 7/2003 | Estes | .................. | A61M 16/0051 128/204.18 |
| 2005/0115561 A1* | 6/2005 | Stahmann | ............. | A61B 5/0031 128/200.24 |
| 2005/0190062 A1* | 9/2005 | Sullivan | ............... | A61B 5/0205 340/573.1 |
| 2005/0217674 A1* | 10/2005 | Burton | ..................... | A61B 5/04 128/204.23 |
| 2007/0073169 A1* | 3/2007 | Averina | ............... | A61B 5/0816 600/483 |
| 2007/0213624 A1* | 9/2007 | Reisfeld | ............... | A61B 5/0402 600/504 |
| 2008/0275349 A1* | 11/2008 | Halperin | ............... | A61B 5/0205 600/484 |
| 2010/0076514 A1* | 3/2010 | Cho | ..................... | A61B 5/0031 607/18 |

\* cited by examiner

PATIENT MONITORING AND EXCEPTION NOTIFICATION

This patent application claims the priority benefit under 35 U.S.C. § 371 of international patent application no. PCT/IB2011/055781, filed Dec. 19, 2011, which claims the priority benefit under 35 U.S.C. § 119(e) of U.S. Provisional Application No. 61/425,827 filed on Dec. 22, 2010, the contents of which are herein incorporated by reference.

BACKGROUND OF THE INVENTION

1. Field of the Invention

The invention relates to automated patient (or subject) monitoring. A user of the invention, e.g. a clinician, may wish to be notified when the condition of a subject has changed and/or is expected to change.

2. Description of the Related Art

Patients (or subjects) may be monitored, e.g. at their home, by taking measurements at different moments in time. For example, subjects may be asked to weigh themselves every day and report to their physician if they notice a significant change in weight. The measurements may be compared to a threshold, e.g. determined by a physician, such that a notification is only required when a measurement exceeds the threshold.

SUMMARY OF THE INVENTION

One aspect of the disclosure relates to a method for providing exception notification on behalf of a subject. In one embodiment, the method comprises recording a plurality of subsequent measurements for a subject of one or more breathing parameters; determining a statistical metric of the recorded plurality of subsequent measurements; verifying whether the statistical metric warrants a notification on behalf of the subject to the user based on configuration settings; and conveying the notification on behalf of the subject to the user.

Another aspect of the disclosure relates to a system for providing exception notification on behalf of a subject. In one embodiment, the system comprises a measurement device, a user interface, electronic storage, and a processor. The measurement device is configured to measure for a subject one or more breathing parameters. The user interface is configured to exchange information with a user, wherein the information includes notifications. The electronic storage stores measurements from the measurement device. The processor is configured to execute computer program modules including a statistical module, a verification module, and a user interface module. The statistical module is configured to determine a statistical metric of the measurements measured by the measurement device. The verification module is configured to verify whether the determined statistical metric warrants a notification on behalf of the subject based on configuration settings. The user interface module is configured to control the user interface to convey the notification on behalf of the subject to the user.

Yet another aspect of the disclosure relates to a system configured to provide exception notification on behalf of a subject. In one embodiment, the system comprises means for recording a plurality of subsequent measurements for a subject of one or more breathing parameters; means for determining a statistical metric of the recorded plurality of subsequent measurements; means for verifying whether the statistical metric warrants a notification on behalf of the subject to the user based on configuration settings; and means for conveying the notification on behalf of the subject to the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
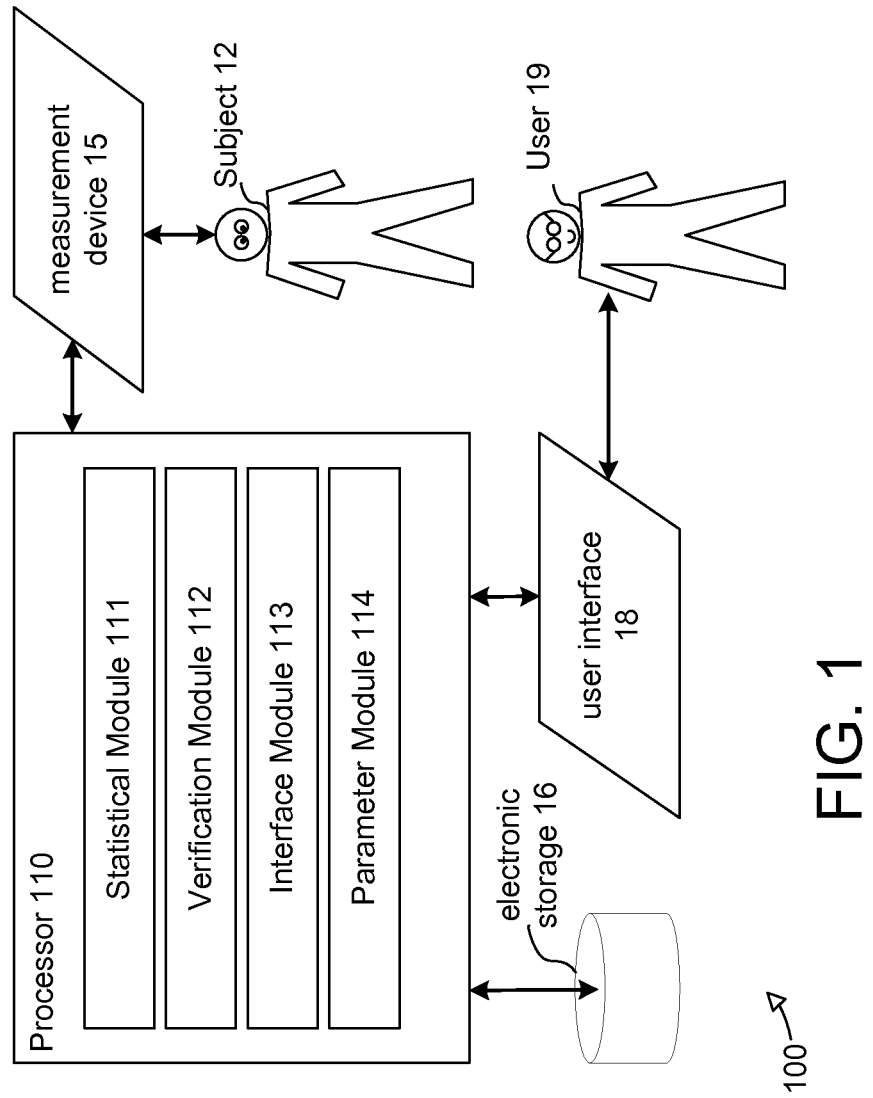
FIG. 1 illustrates an exemplary implementation of a patient monitoring system, a subject, and a user.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates an exemplary implementation of a patient monitoring system 100, a subject 12, and a user 19. System 100 may be configured to provide exception notification on behalf of subject 12. Exception notification may mean a notification is provided in case one or more particular conditions are met. For example, the conditions may pertain to the physical well-being of a patient (or subject)

receiving treatment at home, and the notification may be provided to a clinician (or user) who is monitoring the patient at risk for developing specific problems that require hospitalization. An exception, thus, may mean the medical condition of a patient does not conform to the general rules or expectations for the patient's well-being. In one embodiment, system 100 includes one or more of a measurement device 15, electronic storage 16, user interface 18, processor 110, and/or other components.

In one embodiment, measurement device 15 is configured to measure for a subject one or more of an apnea-hypopnea index, a tidal volume, a percentage of breaths taken using assisted respiration, and/or other quantifiers of the physical well-being of a subject. Measurement device 15 may include one or more sensors that generate output signals used to determine measurements. The sensor output signals may be transformed into sensor output values by an executable computer program module, a constituent part of the sensor, a constituent part of measurement device 15, and/or a component of system 100 or a constituent part thereof. Measurement device 15 may perform measurements every second, every minute, every hour, every day, every week, multiple times per second, multiple times per hour, multiple times per day, multiple times per week, at other regular intervals, as prompted by the user, and/or according to any schedule.

The sensor output signals and/or the sensor output values may be recorded and/or stored for analysis in electronic storage 16 and/or elsewhere. A measurement device configured to record a plurality of subsequent measurements for a subject of one of either an apnea-hypopnea index, a tidal volume, a percentage of breaths taken using assisted respiration, and/or other breathing parameters may be known to those in the art of assisted respiration, in particular as related to patients using an appliance for non-invasive mechanical ventilation.

By way of non-limiting example, measurement device 15 may be included in a pressure generator, a subject interface and/or any other component of a mechanical ventilation system configured to control the pressure of a pressurized flow of breathable gas to provide pressure support to the airway of subject 12. Examples of such an appliance may be a CPAP device, an auto servo ventilation (ASV) device, and/or other devices. As such, the appliance may include a pressure generator, a respiratory circuit, and/or other components. The pressure generator may be configured to generate the pressurized flow of breathable gas for delivery to the airway of subject 12. The pressure generator may control one or more parameters of the pressurized flow of breathable gas in accordance with a therapy regimen. The one or more parameters may include, for example, pressure, flow rate, temperature, humidity, velocity, acceleration, gas composition, acoustics, changes in a parameter indicative of respiration, gas parameters and/or other parameters.

The respiratory circuit may be configured to deliver the pressurized flow of breathable gas from the pressure generator to the airway of subject 12. The respiratory circuit may include a conduit and a subject interface appliance. The conduit may place the subject interface appliance in fluid communication with the pressure generator. The subject interface appliance is configured to engage subject 12 to deliver the pressurized flow of breathable gas. The subject interface appliance may be invasive or non-invasive. The subject interface appliance may include, for example, a nasal cannula, a nasal mask, a nasal/oral mask, a full face mask, a total face mask, air outlet, or other interface appliances that communication a flow of gas with an airway of a subject, and/or other appliances.

In one embodiment, subject 12 is monitored by a positive airway pressure device, or other device including measurement device 15, at home for quantifiable symptoms, e.g. related to respiration, of congestive heart failure and/or other conditions. The measurement device 15 may generate output signals related to respiratory and/or sleep parameters of subject 12 indicating a worsening of the condition or a change in response to medication. A clinician (e.g. user 19) may wish to be notified in such a circumstance.

In one embodiment, electronic storage 16 comprises storage media that electronically store information. The electronic storage media of electronic storage 16 may include one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 110, information received via user interface 18 and/or measurement device 15, and/or other information that enables system 100 to function properly. Electronic storage 16 may be (in whole or in part) a separate component within system 100, or electronic storage 16 may be provided (in whole or in part) integrally with one or more other components of system 100 (e.g., measurement device 15, user interface 18, processor 110, etc.).

User interface 18 is configured to provide an interface between system 100 and subject 12 and/or user 19 (e.g. a clinician, a caregiver, a doctor, a researcher, a therapy decision-maker, and/or other users) through which a user may exchange information with system 100. This enables data, cues, results, configuration settings, and/or instructions and any other communicable items, collectively referred to as "information," to be communicated between a user and one or more of measurement device 15, electronic storage 16, and/or processor 110. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with measurement device 15.

It is to be understood that other communication techniques, either hard-wired or wireless, are also contemplated as user interface 18. For example, user interface 18 may be integrated with a removable storage interface provided by electronic storage 16. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 18 include, but are not limited to, an RS-232 port, RF link, an IR link, modem (telephone, cable, Ethernet, internet or other). In short, any technique for communicating information with system 100 is contemplated as user interface 18.

Processor 110 is configured to provide information processing capabilities in system 100. As such, processor 110 may include one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 may include a plurality of processing units. These processing units may be physically located within the same device (e.g., measurement device 15), or processor 110 may represent processing functionality of a plurality of devices operating in coordination.

As is shown in FIG. 1, processor 110 may be configured to execute one or more computer program modules. The one or more computer program modules may include one or more of a statistical module 111, a verification module 112, an interface module 113, a parameter module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. As another example, processor 110 may be configured to execute one or more additional modules that may perform some or all of the functionality attributed below to one of modules 111, 112, 113, and/or 114.

Parameter module 114 may be configured to determine gas and/or breathing parameters and/or indices represented by the sensor output, and/or other parameters represented by the sensor output. Parameter module 114 may operate directly on sensor output signals from one or more sensors included in measurement device 15. Alternatively, and/or simultaneously, parameter module 114 may operate on sensor output values that are represented by sensor output signals. As such, parameter module 114 may operate on sensor output signals and/or sensor output values that are recorded and/or stored in electronic storage 16 or elsewhere. For example, parameter module 114 may determine weekly averages for various breathing parameters that are measured on a daily or nightly basis. As another example, parameter module 114 may determine an apnea-hypopnea index, in part, based on sensor output representing whether an apnea occurred.

Parameter module 114 may further be configured to use measurements from one or more sensors included in measurement device 15 to determine parameters including arousal index, (average) breath rate, (average) percentage of subject-triggered breaths taken, (average) pressure support (e.g. for auto-servo ventilator device), (average) peak flow, snore index, percentage of time spent in Cheyne-Stokes respiration (CSR), central apnea index (CAI), (average) minute ventilation, 90% CPAP or EPAP, (average) breath sound, total sleep time, and/or other quantifiers of patient well-being. A subject in stable medical condition may typically have stable measurements, within a given range of variability. As the medical condition changes, the measurements may change in average/mean values, variability, and/or other statistical metrics.

Statistical module 111 may be configured to determine a statistical metric of measurements from measurement device 15. Statistical module 111 may operate directly on sensor output signals from a constituent part of measurement device 15, signal output values corresponding to those sensor output signals, and/or stored electronic information—e.g. from electronic storage 16—representing either sensor output, one or more parameters determined by parameter module 114, and/or any information based on sensor output and/or other measurements. The statistical metric may be statistical variability of a parameter determined by parameter module 114, trend estimation with respect to a parameter determined by parameter module 114, standard deviation of a parameter determined by parameter module 114, and/or other statistical metrics related to a parameter determined by parameter module 114. The statistical metric may be related to a specific duration of time, e.g. a day, a week, two weeks, four weeks, a month, and/or other durations of time. The statistical metric related to a specific duration of time may be based on multiple measurements taken during the specific duration of time. For example, the statistical metric may be the standard deviation of a set of measurements spanning no more than two weeks or more than two weeks. Alternatively, the statistical metric may be the standard deviation of a set of measurements spanning less than a day, less than a week, less than two weeks, less than four weeks, less than six months, more than a day, more than a week, more than four weeks, more than six months, and/or other periods. The specific duration of time may be configurable and/or programmable by a user.

By way of non-limiting example, measurement device 15 may measure average tidal volume on a night-by-night basis through a flow sensor included in measurement device 15. The average tidal volume per night—as may be derived by integrating flow sensor output—may be recorded in electronic storage 16 and long term and short term average values and standard deviations may be determined. An example duration for the short term average may be ten days. An example duration for the long term average may be sixty days. If the standard deviation of the short term average is significantly higher than the standard deviation of the long term average, as determined by verification module 112, user 19 may be alerted to a change in the condition of subject 12. Other methods to determine changes in the underlying statistical process of random variables (e.g. the measurements being trended) may be known to those skilled in the art.

In another example, statistical module 111 may be configured to determine a statistical metric of a subject's tidal volume by performing trend estimation on the corresponding measurements spanning a specific duration of time. If the trend or estimated trend breaches a predetermined threshold, a user may wish to be notified on behalf of the subject. For instance, if the trend estimation of a subject's tidal volume decreases by 150 mL or more in a one-week period, a user may wish to be notified on behalf of the subject.

Verification module 112 may be configured to verify whether the statistical metric, as determined by statistical module 111 and optionally based, at least in part, on parameters determined by parameter module 114, warrants a notification on behalf of the subject to the user, wherein the verification is based on configuration settings. In case the statistical metric is statistical variability or standard deviation, verification module 112 may employ configuration settings including a threshold limit and/or other limits to perform its operation. The threshold limit may also vary according to one or more configuration settings, prior measurements, an established baseline, and/or other variables. In case the statistical metric is trend estimation, verification module 112 may perform its operation based on an estimated future measurement of a parameter determined by parameter module 114, a derivative of a set of measurements of a parameter determined by parameter module 114 with respect to time, a threshold limit, a specified change with regard to an established baseline, one or more configuration settings, prior measurements of a parameter determined by parameter module 114, and/or other variables.

The verification performed by verification module 112 with respect to multiple sets of parameters may interact. For example, increased variability on a parameter determined by parameter module 114—such as the apnea-hypopnea index of the subject—may increase the minimum threshold limit for another parameter determined by parameter module 114—such as the average tidal volume of the subject over a particular period. The configuration settings used by verification module 112 may be adjusted, e.g. (remotely) by user 19. Operation of verification module 112 may be based on information that is supplied directly and/or manually by subject 12 and/or user 19, e.g. weight and/or survey information.

Interface module 113 may be configured to control user interface 18 to exchange information with user 19, for example to convey a notification on behalf of subject 12 to user 19. Exchanging information may include controlling user interface 18 to present and/or display any information—such as a notification to a user. Alternatively, and/or simultaneously, interface module 113 may be configured to receive user commands, configuration settings, adjustments to configuration settings, information supplied by subject 12, and/or other received information that affects operation of one or more computer program modules and/or one or more components in system 100. For example, the operation of verification module 112 may be adjusted by using adjusted configuration settings received by interface module 113.

In one embodiment, the step of conveying a notification to a user, as performed by interface module 113, includes bringing the subject's record forward in a database. Simultaneously, and/or alternatively, the notification may include email and/or a text message. Other methods, such as having system 100 upload information automatically to a database, and/or placing a phone call are also envisioned.

Figure 2:
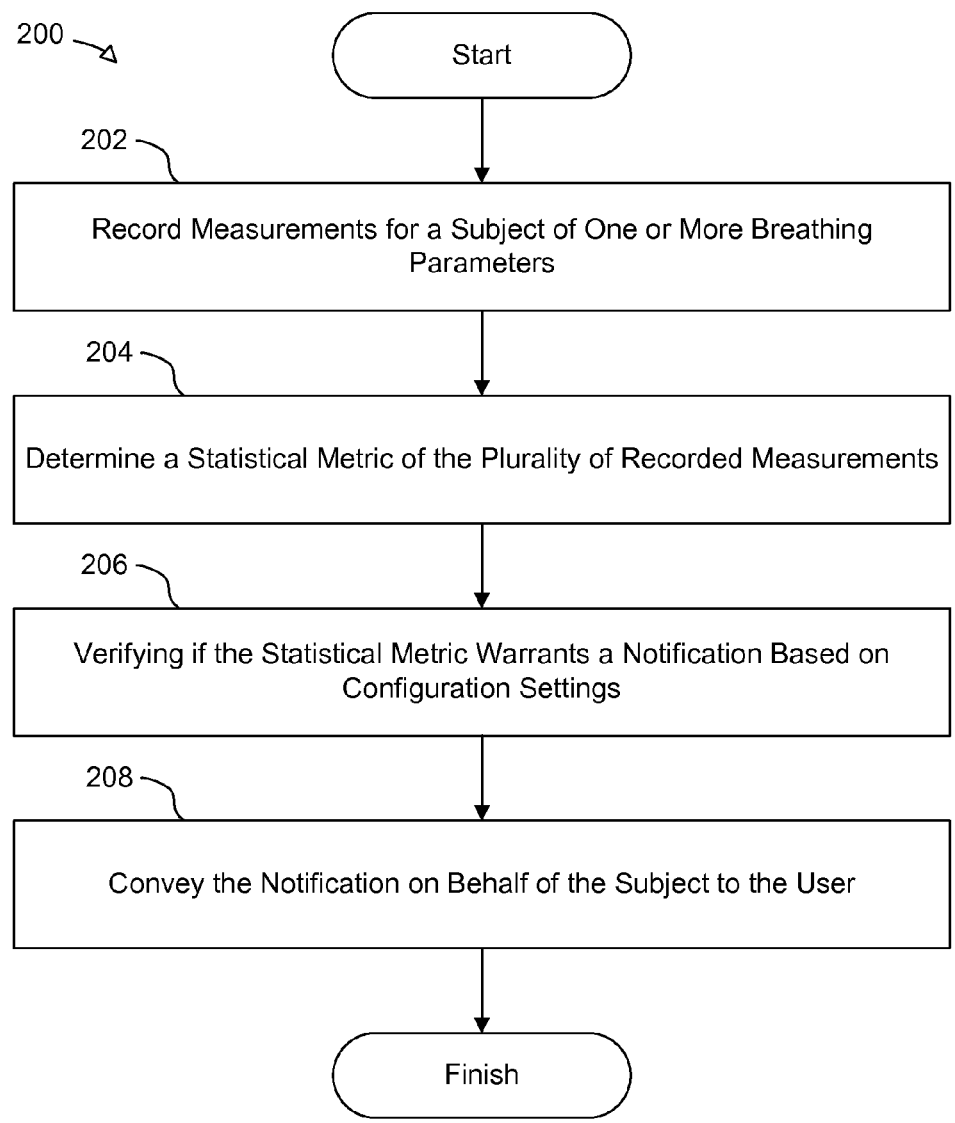
FIG. 2 illustrates an exemplary method for monitoring a subject and providing exception notification, in accordance with one or more embodiments of the present invention.

FIG. 2 illustrates an exemplary method 200 for monitoring a subject and providing exception notification, in accordance with one or more embodiments of the present invention. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium, e.g. an electronic storage medium substantially similar to or the same as electronic storage 16 in FIG. 1. The one or more processing devices may include one or more devices configured through hardware, firmware, and/or software to be specifically designed for execution of one or more of the operations of method 200.

At an operation 202, measurements are recorded for a subject of one or more of an apnea-hypopnea index, a tidal volume, a percentage of breaths taken using assisted respiration, and/or other breathing parameters. In one embodiment, operation 202 is performed by a measurement device substantially similar to or the same as measurement device 15 (shown in FIG. 1 and described above), optionally in cooperation with a parameter module substantially similar to or the same as parameter module 114 (shown in FIG. 1 and described above).

At an operation 204, a statistical metric is determined of the plurality of recorded measurements and/or of parameters derived from measurements. In one embodiment, operation 204 is performed by a statistical module substantially similar to or the same as statistical module 111 (shown in FIG. 1 and described above), optionally in cooperation with a parameter module substantially similar to or the same as parameter module 114 (shown in FIG. 1 and described above).

At an operation 206, it is verified whether the statistical metric warrants a notification to a user, based on configuration settings. In one embodiment, operation 206 is performed by a verification module substantially similar to or the same as verification module 112 (shown in FIG. 1 and described above).

At an operation 208, the notification is conveyed on behalf of the subject to the user. In one embodiment, operation 208 is performed by an interface module substantially similar to or the same as interface module 113 (shown in FIG. 1 and described above) is cooperating with a user interface substantially similar to or the same as user interface 18 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination Although the description for the purpose of illustration is based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for providing dynamic-threshold-based exception notifications on behalf of a subject, the method comprising:
periodically measuring, with a medical device attached to the subject for periodically measuring the subject's respiration, a plurality of subsequent measurements of breathing parameters of the subject during a first period and a second period, the breathing parameters including a first and a second breathing parameter, wherein the first breathing parameter is an average tidal volume of the subject and the second breathing parameter is an apnea-hypopnea index of the subject;
determining, with a processor, statistical metrics of the measured plurality of subsequent measurements, wherein the statistical metrics include:
a first statistical metric corresponding to measurements taken during the first period, wherein the first statistical metric includes trend estimation of the measurements during the first period; and
a second statistical metric subsequent to the first statistical metric corresponding to measurements taken during the second period, wherein the second statistical metric includes trend estimation of the measurements during the second period, and wherein the second period is longer than the first period;
automatically adjusting a breathing parameter threshold for the measured first breathing parameter, wherein the breathing parameter threshold is a threshold of average tidal volume, such that the breathing parameter threshold changes from a first threshold value at a first time during the first period to a second threshold value at a second time during the first period or the second period, wherein the automatically adjusting includes increasing the breathing parameter threshold in response to an increase in variability of the measured second breathing parameters in the first period and/or the second period;
verifying, with a processor, whether the statistical metrics warrant a notification on behalf of the subject to a user based on (i) the automatically-adjusted breathing parameter threshold at a given time during the first period and (ii) a comparison between the first statistical metric and the second statistical metric; and
conveying, via a user interface, the notification on behalf of the subject to the user.

2. The method of claim 1, wherein the statistical metrics include statistical variability of the parameters.

3. The method of claim 1, wherein the statistical metrics include a first standard deviation for a set of measurements measured during the first period spanning less than two weeks, and a second standard deviation for a set of measurements measured during the second period spanning more than two weeks, and wherein verifying whether the statistical metrics warrant a notification includes comparing the first standard deviation and the second standard deviation.

4. A system for providing dynamic-threshold-based exception notification on behalf of a subject, the system comprising:
a medical device attached to the subject configured to periodically measure subsequent measurements of breathing parameters of the subject during a first period and a second period, the breathing parameters including a first and second breathing parameters, wherein the first breathing parameter is an average tidal volume of the subject and the second breathing parameter is an apnea-hypopnea index of the subject;
a user interface configured to exchange information with a user, wherein the information includes notifications;
electronic storage to store measurements from the measurement device; and
a processor configured to execute computer program modules, the computer program modules comprising:
a statistical module configured to determine statistical metrics of the subsequent measurements measured by the medical device, wherein the statistical metrics include:
a first statistical metric corresponding to measurements taken during the first period, and wherein, the first statistical metric includes trend estimation of the measurements during the first period; and
a second statistical metric subsequent to the first statistical metric corresponding to measurements measured during the second period, wherein the second period is longer than the first period, and wherein the second statistical metric includes trend estimation of the measurements during the second period;
a verification module configured to
automatically adjusting a breathing parameter threshold for the measured first breathing parameter, wherein the breathing parameter threshold is a threshold of average tidal volume, such that the breathing parameter threshold changes from a first threshold value at a first time during the first period to a second threshold value at a second time during the first period or the second period, wherein the automatically adjusting includes increasing the breathing parameter threshold in response to an increase in variability of the measured second breathing parameters in the first period and/or the second period; and
verify whether the determined statistical metrics warrant a notification on behalf of the subject based on (i) the automatically-adjusted breathing parameter threshold at a given time during the first period and (ii) a comparison between the first statistical metric and the second statistical metric; and
a user interface module configured to control the user interface to convey the notification on behalf of the subject to the user.

5. The system of claim 4, wherein the statistical metrics determined by the statistical module include statistical variability of the parameters.

6. The system of claim 4, wherein the statistical metrics determined by the statistical module include a first standard deviation for a set of measurements measured during the first period spanning less than two weeks, and a second standard deviation for a set of measurements measured during the second period spanning more than two weeks, and wherein operation of the verification module is further based on a comparison between the first standard deviation and the second standard deviation.

7. A system configured to provide dynamic-threshold-based exception notification on behalf of a subject, the system comprising:
means for periodically measuring a plurality of subsequent measurements of breathing parameters of the subject during a first period and a second period, the breathing parameters including a first and second breathing parameters, wherein the first breathing parameter is an average tidal volume of the subject and the second breathing parameter is an apnea-hypopnea index of the subject;

means for determining statistical metrics of the measured plurality of subsequent measurements, wherein the statistical metrics include:
- a first statistical metric corresponding to measurements taken during the first period, and wherein, the first statistical metric includes trend estimation of the measurements during the first period; and
- a second statistical metric subsequent to the first statistical metric corresponding to measurements measured during the second period, wherein the second statistical metric includes trend estimation of the measurements during the second period, and wherein the second period is longer than the first period;

means for automatically adjusting a breathing parameter threshold for the measured first breathing parameter, wherein the breathing parameter threshold is a threshold of average tidal volume, such that the breathing parameter threshold changes from a first threshold value at a first time during the first period to a second threshold value at a second time during the first period or the second period, wherein the automatically adjusting includes increasing the breathing parameter threshold in response to an increase in variability of the measured second breathing parameters in the first period and/or the second period; and means for verifying whether the statistical metrics warrant a notification on behalf of the subject to a user based on (i) the automatically-adjusted breathing parameter threshold at a given time during the first period and (ii) a comparison between the first statistical metric and the second statistical metric; and means for conveying the notification on behalf of the subject to the user.

8. The system of claim 7, wherein the statistical metrics include statistical variability of the parameters.

9. The system of claim 7, wherein the statistical metrics include a first standard deviation for a set of measurements measured during the first period spanning less than two weeks, and a second standard deviation for a set of measurements measured during the second period spanning more than two weeks, and wherein the operation of the means for verifying the statistical metrics warrant a notification includes comparing the first standard deviation and the second standard deviation.

* * * * *